(12) United States Patent
Fort et al.

(10) Patent No.: US 7,855,785 B2
(45) Date of Patent: Dec. 21, 2010

(54) FLUORESCENCE DETECTION DEVICE

(75) Inventors: Emmanuel Fort, Paris (FR); Sandrine Leveque-Fort, Paris (FR); Eric Le Moal, Saint Cyr l'ecole (FR); Marie-Pierre Fontaine-Aupart, Fresnes (FR); Christian Ricolleau, Paris (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 658 days.

(21) Appl. No.: 11/817,664

(22) PCT Filed: Mar. 2, 2006

(86) PCT No.: PCT/IB2006/000647
§ 371 (c)(1),
(2), (4) Date: Aug. 31, 2007

(87) PCT Pub. No.: WO2006/092735
PCT Pub. Date: Sep. 8, 2006

(65) Prior Publication Data
US 2008/0158559 A1    Jul. 3, 2008

(30) Foreign Application Priority Data
Mar. 3, 2005    (EP)    ................... 05290480

(51) Int. Cl.
*G01J 3/30*    (2006.01)
(52) U.S. Cl. ...................... 356/317; 356/311
(58) Field of Classification Search ................. 356/317, 356/445, 311, 300, 417, 948, 949; 250/483.1, 250/487.1, 488.1, 486.1, 458.1, 459.1, 461.2, 250/465.1, 466.1; 436/171, 172, 518, 519, 436/524, 164, 805, 807; 435/287.1, 287.9, 435/288.7; 385/129, 131
See application file for complete search history.

(56) References Cited

U.S. PATENT DOCUMENTS

| 4,649,280 | A | | 3/1987 | Holland et al. |
| 5,006,716 | A | | 4/1991 | Hall |
| 5,841,143 | A | * | 11/1998 | Tuma et al. ............... 250/458.1 |
| 5,866,433 | A | | 2/1999 | Schalkhammer et al. |
| 2004/0165187 | A1 | * | 8/2004 | Koo et al. .................... 356/445 |
| 2004/0246485 | A1 | | 12/2004 | Imani et al. |

OTHER PUBLICATIONS

Lévêque-Fort, S. et al. (2004). "Nanostrucutred Thin Films for Fluorescence Enhancement," Proceedings of SPIE Conference, *Plasmonics in Biology and Medicine* 5327:29-36.

* cited by examiner

*Primary Examiner*—Gregory J Toatley
*Assistant Examiner*—Tri T Ton
(74) *Attorney, Agent, or Firm*—Baker Donelson Bearman, Caldwell & Berkowitz, PC

(57) ABSTRACT

This invention relates to a fluorescence detection device comprising a support means (101) for supporting a sample (111), a sample excitation means so that a fluorescence is emitted by the sample (111) and a detection means for detecting said fluorescence, said support means (101) comprising a layer having a rough surface (115) for redirecting said fluorescence in a plurality of directions and said detection means covering an observation cone to collect the redirected fluorescence in a plurality of directions.

25 Claims, 4 Drawing Sheets

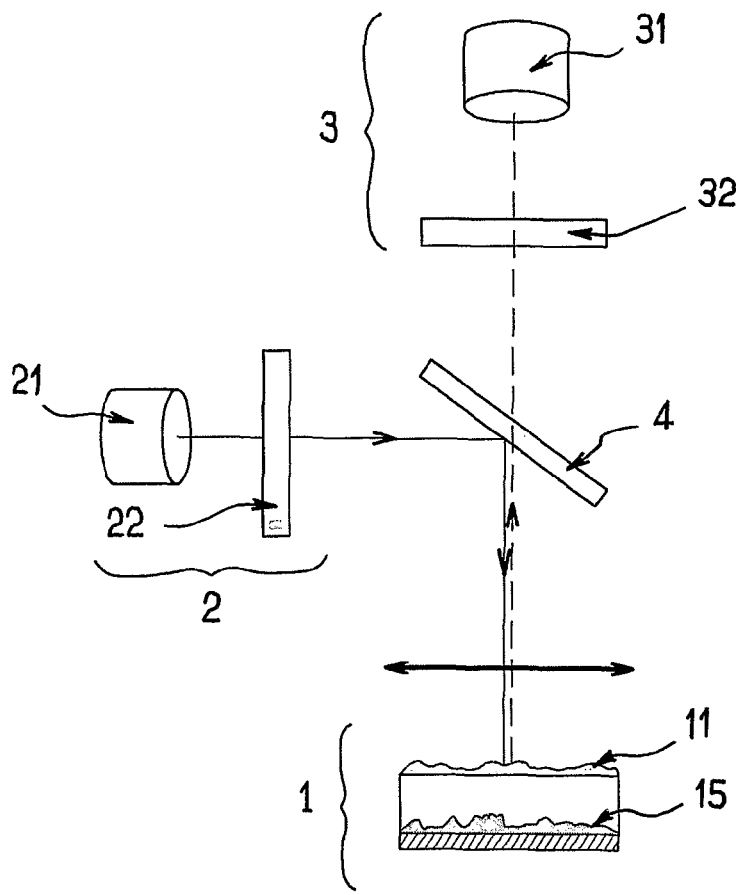
FIG_1
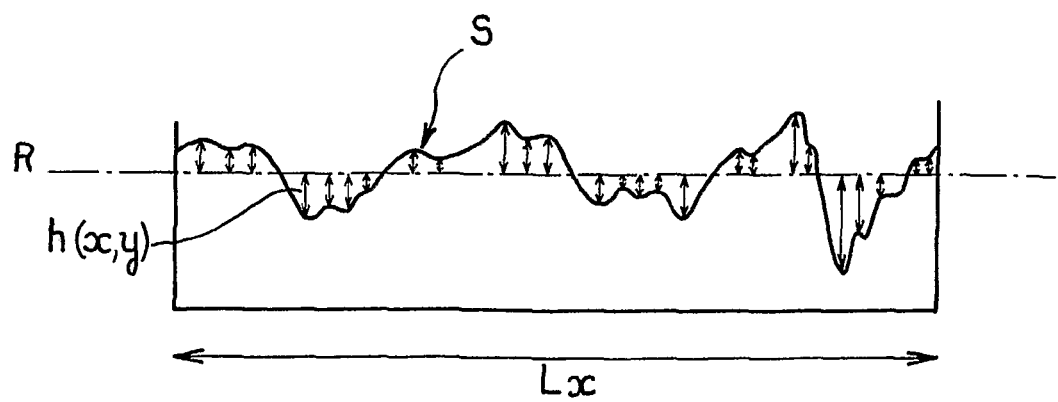
FIG_2

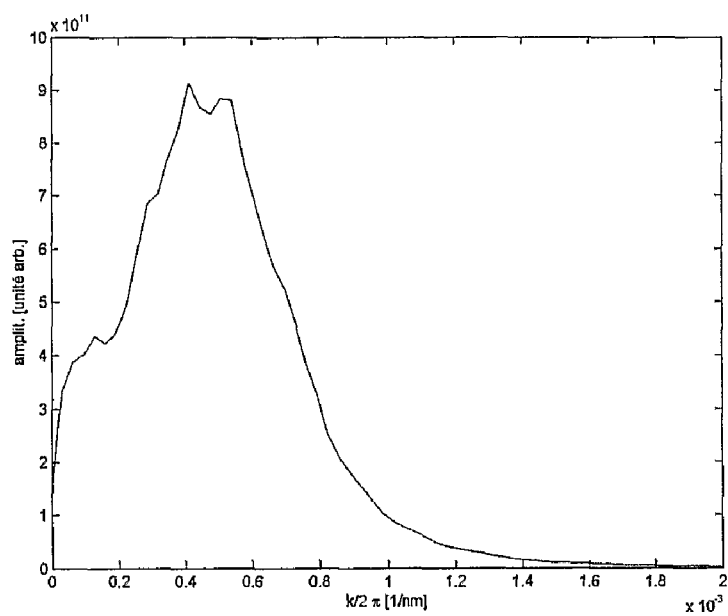
FIG_4
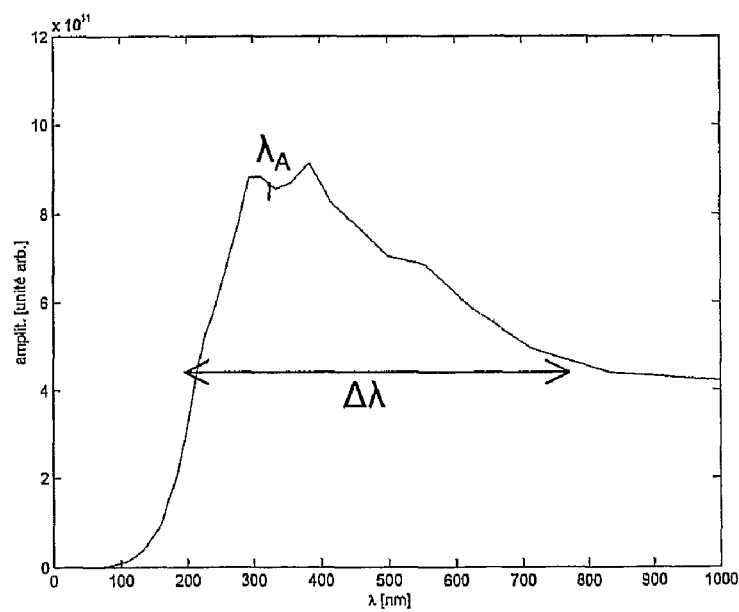
FIG.5

FLUORESCENCE DETECTION DEVICE

CROSS REFERENCE TO RELATED APPLICATIONS

This is a §371 National Stage Application of International Application No. PCT/IB2006/000647 filed Mar. 2, 2006, which claims priority from European Application No. 05290480.2 filed Mar. 3, 2005.

BACKGROUND OF THE INVENTION

1. Field of the Invention

This invention relates to the field of spectroscopy, and more particularly fluorescence imaging.

2. Description of Related Art

Many studies and applications make use of a fluorescence signal, particularly in biology. The weakness of the fluorescence signal is a major technical stumbling block. In most applications and studies, the quantity of fluorescent markers or fluorophores is namely often limited. It is important to increase sensitivity in the case of biochips for example, or when monitoring small quantities of molecules in cells. The increase of the fluorescence signal is also sought for molecules with a low fluorescence quantum efficiency.

At the moment, needs are essentially satisfied by specific observation techniques, and particularly lighting techniques using evanescent waves in total reflection. Furthermore, the weakness of the fluorescence signal makes it necessary to use additional amplification techniques, frequently expensive, requiring a large amount of time and introducing amplification biases that have to be controlled. A typical case is DNA chips for which a polymerase chain reaction (PCR) amplification step is often essential. Many types of supports have been developed to enhance the fluorescence signal and minimise the need for such an amplification step.

Some supports as those described in U.S. Pat. No. 5,866,433 are based on enhanced fluorescence induced by the presence of metallic nanoparticles under a transparent and inert separating layer.

There are also mirror type supports with a transparent spacing layer, Supports proposed in U.S. Pat. No. 4,649,280 are perfect mirrors covered with a transparent spacing layer. U.S. Pat. No. 5,006,716 proposes mirrors with a periodically corrugated conducting layer so as to induce fluorescence in a preferential direction, therefore requiring excitation and detection along a clearly defined direction. Therefore specific excitation and observation configurations are necessary to use this type of support.

However all these supports that enable a certain enhancement of the fluorescence signal have a number of disadvantages, particularly related to the specific nature of the detection devices or their particular usage configuration. Thus, the use of such supports remains complex and/or expensive.

Therefore it is an object of the invention to provide a simplified fluorescence detection device that at least overcomes at least one of the above-mentioned disadvantages.

SUMMARY OF THE INVENTION

Consequently the invention consists of a fluorescence detection device as defined below in the claims.

More precisely, there is provided a fluorescence detection device that comprises a support means for supporting a sample, a sample excitation means so that a fluorescence is emitted by the sample and a detection means for detecting said fluorescence, characterised in that said support means comprises a layer having a rough surface for redirecting said fluorescence in a plurality of directions and said detection means covers an observation cone to collect the redirected fluorescence in a plurality of directions.

Therefore, such a device will lead to an enhancement of the fluorescence signal originating from the excited fluorophore (s) of the sample, said fluorescence signal being emitted within a broad transmission lobe rather than in a preferred direction. Thus detection over a wide aperture makes it possible to collect most of the fluorescence signal. Therefore the collected fluorescence signal will be enhanced without any prior amplification and/or use of a particular detection system or in a particular configuration.

The rough surface of the layer of the support means has a roughness defined by at least three parameters, a first parameter representing the standard deviation of roughness, a second parameter representing the average spatial period of roughness and a third parameter representing the range of spatial periods of roughness. The second and third parameters are derived from the radial profile of the power spectrum of the rough interface topography image. The first parameter is non-zero and less than 100 nanometers (nm), the second parameter is non-zero and less than 1000 nm and the third parameter is non-zero and less than 1500 nm.

Preferred but non-limitative aspects of the fluorescence detection device according to the invention are as follows:
- the observation cone is defined by an apex angle of at least 10 degrees;
- the layer having a rough surface is continuous or quasi-continuous;
- the layer having a rough surface is a conducting layer;
- the conducting layer is a metallic layer, made of silver, gold, copper, aluminium or platinum;
- the conducting layer is a semi-conductor;
- the conducting layer is more than 20 nm thick;
- the support means includes a spacing layer transparent to the excitation and emission wavelengths involved in the fluorescence process;
- the spacing layer is a layer of polymers or a ceramic layer;
- the spacing layer is more than 20 nm thick;
- the spacing layer is about 60 nm thick, the conducting layer is about 60 nm thick and the roughness of the surface of the conducting layer is defined by a first parameter of about 20 nm, a second parameter of about 350 nm and a third parameter of about 600 nm,
- the spacing layer is arranged according to a thickness gradient and is increasing from a first end of the support means to a second end of the support means;
- the excitation means covers an illumination cone.

The fluorescence detection device according to the invention is to be used for monitoring fluorophores in a sample. It could in particular be used for the study of inter-fluorophore energy transfers.

Another preferred but non-limitative use of the fluorescence detection device according to the invention concerns measurement of the thickness of transparent samples.

There is further provided a sample support means for a fluorescence detection device according to this invention characterised by the fact that it comprises a layer having a rough surface for redirecting said fluorescence in a plurality of directions.

Finally, this invention relates to a fluorescence detection method including successive steps for excitation of a sample supported by a support means so that a fluorescence is emitted by said sample and for detection of said fluorescence emitted by said excited sample. This fluorescence detection method is characterised in that said support means comprises a layer having a rough surface for redirecting said fluorescence in a plurality of directions and said fluorescence detection step comprises an observation within a cone to collect the redirected fluorescence in a plurality of directions.

DESCRIPTION OF THE DRAWINGS

Other characteristics and advantages of the invention will become clear from the following description which is only given for illustrative purposes and is in no way limitative and should be read with reference to the attached drawings on which:

FIG. 1 shows a diagrammatic view of the fluorescence detection device according to the invention, FIG. 2 shows a sectional view of the profile of a rough surface as defined in the invention, FIG. 4 shows the radial profile of the power spectrum derived from the topography image in FIG. 3 as a function of the spatial frequency, FIG. 5 shows the radial profile of the power spectrum as a function of the spatial periods.

DETAILED DESCRIPTION OF AN EMBODIMENT OF THE INVENTION

Figure 3:
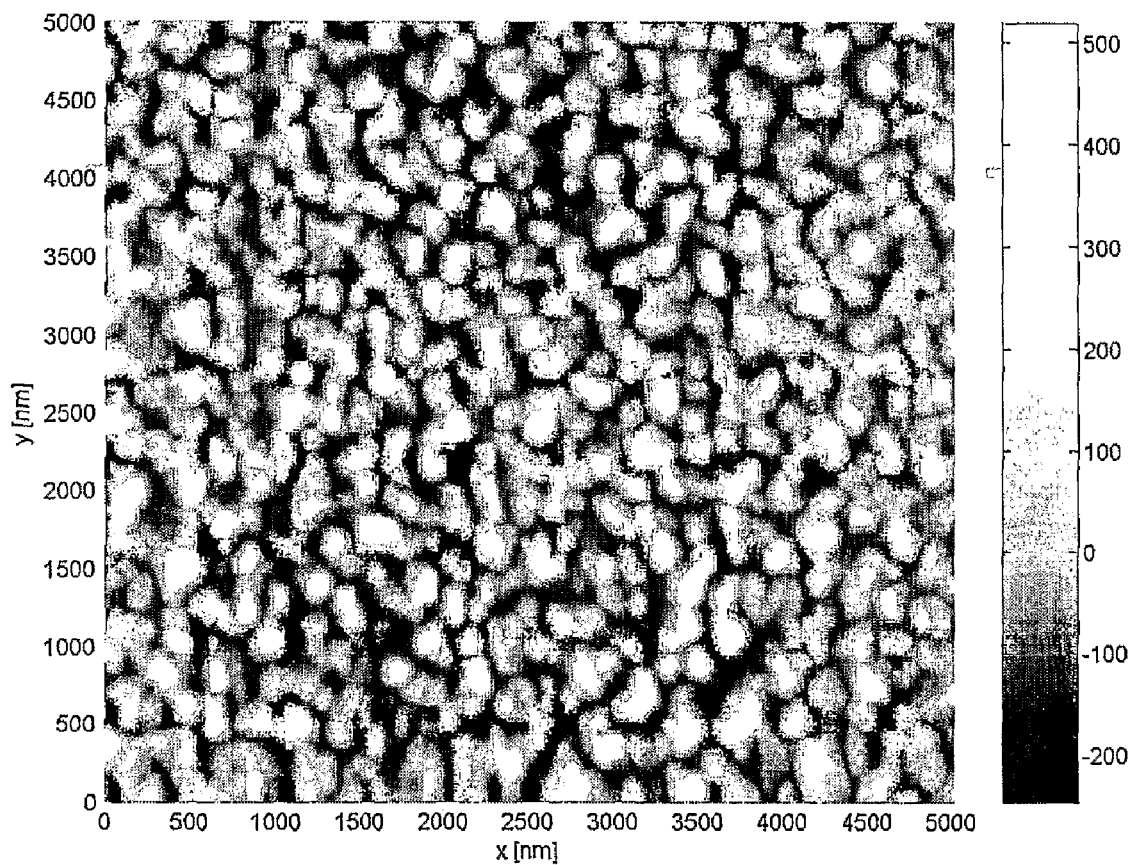
FIG. 3 is an image obtained by atomic force microscopy of the topography of a rough surface.

FIG. 1 shows a diagrammatic view of the fluorescence detection device according to the invention. This device comprises a support means (1) for supporting a sample (11), an excitation means (2) and a fluorescence detection means (3).

The excitation means (2) of the sample (11) is configured so as to excite the fluorophore to be detected in the sample. A fluorophore is namely characterised by two spectra: its incident light absorption spectrum (or excitation spectrum) and its fluorescence emission spectrum. Thus, the excitation means (2) comprises a light source (21) and an excitation filter (22) that enables the excitation means (2) to emit incident radiation at a wavelength corresponding to the absorption spectrum of the fluorophore to be detected. Furthermore, this excitation means (2) may have a range distributed over a solid angle, that is exciting the sample to be analysed according to an illumination cone.

The detection means (3) of the fluorescence detection device is configured so as to only detect fluorescent radiation corresponding to the emission spectrum characteristic of the fluorophore to be detected. Thus, the detection means (3) includes an observation means (31) and an emission filter (32) that only allows transmission of radiation characteristic of the fluorescence to be detected. Furthermore, this detection means (3) covers an observation cone and thus enables detection of radiation emitted in a large number of directions. This observation cone may be defined by an apex angle of at least 10 degrees.

The fluorescence detection device also comprises a dichroic mirror (4) reflecting incident radiation towards the sample and only allowing transmission of radiation characteristic of the fluorescence emitted by the fluorophore to be detected.

For example, the optical system geometry for use of the support (1) may be the one of standard, confocal, monophotonic or biphotonic fluorescence microscopes or the one of scanners.

Further, the support (1) being manufactured to self-enhance the emitted fluorescence, the use of immersion objectives (water, oil) is not necessary anymore. Therefore, the self-enhancement allowed by the support (1) makes possible the use of simple air objectives, which is particularly advantageous when the use of an immersion objective is complex or fastidious.

FIGS. 2, 3, 4 and 5 illustrate parameters chosen to define the roughness of a surface.

Statistical parameters that characterise the topography of a surface (S) are determined with reference to a reference plane (R). The position of this reference plane (R) corresponds to the average of the heights of the different surface points. FIG. 2 shows a profile representing a one dimension view of the surface topography. This profile demonstrates the first parameter used, namely the standard deviation of roughness $\partial$ that characterises the profile in height. This parameter corresponds to the root mean square of the value of the differences $h(x,y)$ of the profile from the reference plane (R), that is:

$$\partial = \left( \frac{1}{L_x L_y} \int_0^{L_x} \partial x \int_0^{L_y} (h(x, y))^2 \partial y \right)^{1/2}$$

where $L_x$ and $L_y$ are the dimensions of the rough interface being analysed and $h(x,y)$ is the height of the surface above the reference plane (R) at the position $(x,y)$.

Moreover, the roughness will be defined by two parameters $\lambda_A$ and $\Delta\lambda$ that characterise the roughness in the plane of the surface. This pair of parameters is determined from the power spectrum derived from the image of the topography of the rough surface being analysed. Observation of a rough surface by atomic force microscopy (AFM) can result in an image of its topography as shown in FIG. 3. Starting from this image of the surface topography, it is possible to work on the power spectrum corresponding to the norm of the Fourier transform of the image. This new representation is equivalent to a surface decomposition based on the sinusoidal functions along a given direction. Since a rough surface does not have a preferred direction, its spectral representation will not have one either. It is then possible to only consider the radial profile of the power spectrum as shown in FIG. 4. The surface roughness is essentially composed of the spatial frequencies having a significant value on the radial spectrum. It is also possible to represent the radial profile as a function of the spatial periods $\lambda$, as shown in FIG. 5. The spectral band $\Delta\lambda$ is defined at mid-height of the maximum of the radial profile. This spectral band $\Delta\lambda$ of a radial profile demonstrates the different wavelengths of ripples making up the surface. The average value $\lambda_A$ of the spatial periods and the spectral band $\Delta\lambda$ will therefore be sufficient to precisely define the surface roughness.

The different roughness characterisation parameters having been defined, a more detailed description of the supports (1) used to increase the fluorescence signal has to be made. Important features for enhancement of fluorescence reside in the presence of a conducting layer that must be covered by a spacing layer, and on the presence of a rough interface.

The spacing layer must be transparent to the wavelengths involved in the fluorescence process, that is the excitation and emission wavelengths of the fluorophore to be detected, in order to enable the electromagnetic radiation to reach the conducting layer. The thickness of this spacing layer is typically a few tens of nanometers (nm) and may be adjusted for given fluorophore and excitation wavelength. This spacing layer may be a polymer layer (PPMA, PEG, etc.), or a ceramic layer ($SiO_2$, $Al_2O_3$, $TiO_2$, etc.). The sample itself may also compose this spacing layer when the objective for example is to observe biological molecules; the lipidic layer, the cellular membrane, etc. of samples would thus form a spacing layer. In the latter case, it will not be necessary to use a support including a spacing layer.

The nature of the conducting layer is not critical. For example, it may be composed of a metal such as gold, silver, copper, aluminium or platinum. The conducting layer could alternatively be a semi-conductor. This layer must be continuous or quasi-continuous, but its thickness is not critical. By continuous, one refers to a layer that totally covers the active surface of the support regarding fluorescence. A quasi-continuous layer is a layer having very small imperfections so that it does not strictly cover the whole active surface of the support.

The plasmon excitation phenomenon that exists at the interface between the conducting layer and the spacing layer might cause a loss of energy of the fluorescent radiation and thus an attenuation of the detected fluorescence signal. Nevertheless a coupling between plasmons and propagative electromagnetic waves through the surface roughness may transfer this energy to the fluorescence signal. Therefore the support (1) further comprises a rough interface (15) so that such coupling can occur in order for the resulting enhanced fluorescence signal to be detected by the detection means (3). The roughness of this interface is defined by a standard deviation of roughness $\partial$ being non-zero and equal to a few tens of nanometers and by parameters $\lambda_A$ and $\Delta\lambda$ being non-zero and equal to a few hundreds of nanometers. The isotropic and random nature of the rough surface are also very important since spectral spreading, that is the variety of spatial frequencies present along all directions, is a way for coupling the incident beam with the surface and redirecting the fluorescence emitted by fluorophores of the sample over the entire observation cone covered by the detection means.

Figure 6:
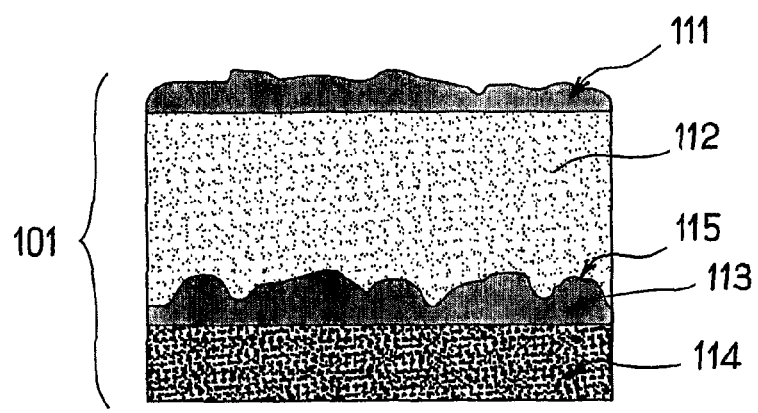
FIG. 6 shows a sectional view of a support according to a first preferred embodiment of the fluorescence detection device.

FIG. 6 shows a support (101) on which the rough interface is the surface (115) of the conducting layer (113). Such a support (101) with a surface (115) of the conducting layer (113) being rough can be made as follows.

The support (101) comprises a substrate (114) on which successive deposits of the conducting layer (113), the spacing layer (112) and the sample (111) are made. Such a substrate (114) could be a glass slide or a silicon wafer.

The conducting layer (113) may be made by a lot of different techniques. By way of example, the surface of the support can be made rough by chemical or mechanical attack, the conducting material deposit being then made by thermal evaporation, laser ablation, electrochemistry, sputtering, etc. In case the support was already conducting, the only step would be to make it rough.

The spacing layer (112), when this latter is not included in the sample to observe, is then deposited on this rough surface (115) by methods similar to the methods used for deposit of the conducting layer. In the case of polymers layers, so called "spin coating" or dip coating" techniques could be used.

In particular, such a support can be prepared under a high vacuum of about $10^{-8}$ torr. A deposit of a 60 nm thick layer of silver is first made by high-temperature evaporation (300° C.) on a clean microscope slide. This first deposit of a few tens of nanometers creates a rough underlayer. A second deposit of a 60 nm thick layer of silver is made at low-temperatures (ambient temperature) in order to form a conducting layer both rough and continuous. The rough surface with a roughness that can be defined by a standard deviation of roughness $\partial$ of about 20 nm, an average spatial period of roughness $\lambda_A$ of about 350 nm and a range of spatial periods of roughness $\lambda_A$ of about 600 nm (between 200 and 800 nm). A 60 nm thick layer of alumina ($Al_2O_3$) is then deposited by pulsed laser ablation at deposit rates of the order of a few nanometers for 100 laser shots, thus forming the spacing layer.

Figure 7:
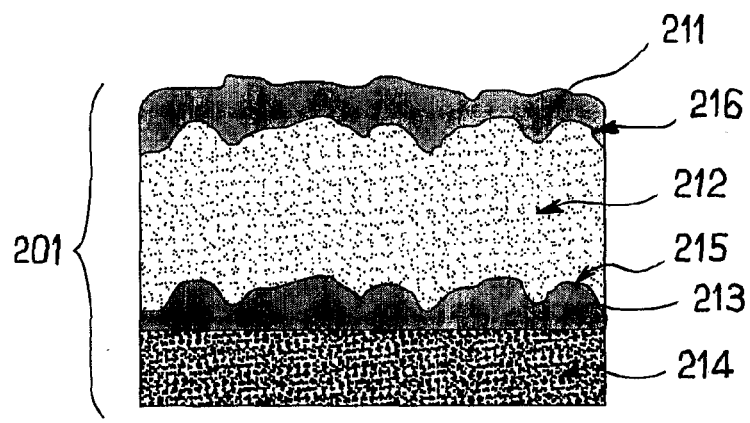
FIG. 7 shows a sectional view of a support according to a second preferred embodiment of the fluorescence detection device.

A support (201), according to another embodiment and according to FIG. 7, will further have a spacing layer (212) having a rough surface (216).

A fluorescence detection device of the type described above will be used in particular for monitoring fluorophores in a sample. In particular could the invention be used for wet or dry biosensors (e.g. biochips) but also for biological or medical imaging (bacteria, cells, membranes, biomolecules, pathologic sections, etc.).

Furthermore, this type of fluorescence detection device could also be used for studying energy transfers such as Fluorescence Resonance Energy Transfers (FRET) that are particularly interesting for biological molecules interactions studies that were often limited by the signal weakness. The support/fluorophore interaction namely modifies the transfer of electromagnetic energy and consequently FRET type processes. The use of a fluorescence detection device according to the invention may thus enhance such processes.

The fluorescence detection device can also be used for measuring the thickness of transparent samples.

Figure 8:
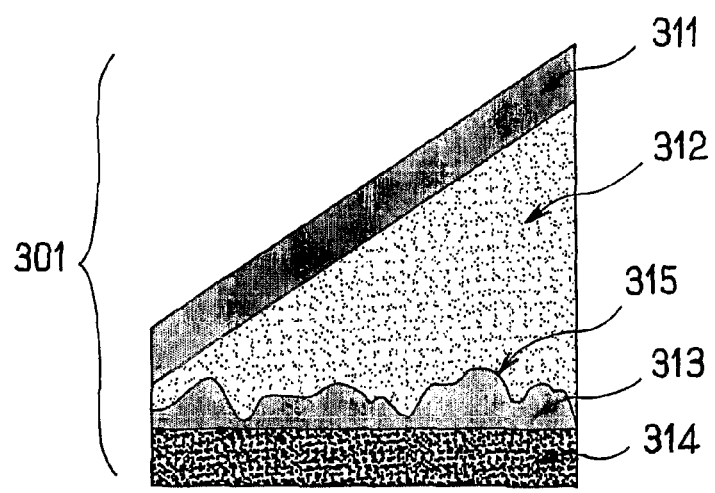
FIG. 8 shows a sectional view of a support according to a third preferred embodiment of the fluorescence detection device.

Enhancement of the fluorescence signal depends on the thickness of the spacing layer. To measure the thickness of a transparent sample, the fluorescence detection device will comprise a support (301) of the type shown in FIG. 8, wherein the surface (315) of the conducting layer (313) is rough and wherein the spacing layer (312) is arranged with a thickness gradient, this thickness increasing from one end of the support to the other. The thickness measurement of a transparent sample will be calculated from the maximum displacement of the fluorescence intensity detected between the support (301) without a transparent sample and the support (301) with the transparent sample (311).

One of the advantages of using such a device is that it can result in a precise thickness measurement without needing to use a specific ellipsometer type instrument.

The reader will have understood that many modifications may be made without going beyond the new information and the advantages described herein. Consequently, all modifications of this type shall be within the scope of the fluorescence detection device and its uses as defined in the attached claims.

The invention claimed is:

1. A fluorescence detection device comprising a support means for supporting a sample, a sample excitation means so that a fluorescence is emitted by the sample and a detection means for detecting said fluorescence, wherein said support mean comprises a layer having a rough surface for redirecting said fluorescence in a plurality of directions and said detection means covers an observation cone to collect the redirected fluorescence in a plurality of directions, and wherein said rough surface has a roughness defined by a standard deviation of roughness and being non-zero and less than 100 nm.

2. The fluorescence detection device according to claim 1, wherein the observation cone is defined by an apex angle of at least 10 degrees.

3. A fluorescence detection device comprising a support means for supporting a sample, a sample excitation means so that a fluorescence is emitted by the sample and a detection means for detecting said fluorescence, wherein said support mean comprises a layer having a rough surface for redirecting said fluorescence in a plurality of directions and said detection means covers an observation cone to collect the redirected fluorescence in a plurality of directions wherein the rough surface has a roughness defined by a range of spatial periods of roughness, said range of spatial periods of roughness being derived from the radial profile of the power spectrum of the topography image of the rough surface, and being non-zero and less than 1500 nm.

4. The fluorescence detection device according to claim 1, wherein the rough surface has a roughness defined by an average spatial period of roughness, said average spatial period of roughness being derived from the radial profile of the power spectrum of the topography image of the rough surface, and being non-zero and less than 1000 nm.

5. The fluorescence detection device according to claim 1, wherein the rough surface has a roughness defined by a range of spatial periods of roughness, said range of spatial periods of roughness being derived from the radial profile of the power spectrum of the topography image of the rough surface, and being non-zero and less than 1500 nm.

6. The fluorescence detection device according to claim 1, wherein the layer having the rough surface is continuous or quasi-continuous.

7. The fluorescence detection device according to claim 1, wherein the layer having the rough surface is a conducting layer.

8. The fluorescence detection device according to claim 7, wherein the conducting layer is a metallic layer.

9. The fluorescence detection device according to claim 8, wherein the metallic layer is made of silver, or gold, or copper, or aluminium, or platinum.

10. The fluorescence detection device according to claim 7, wherein the conducting layer is a semi-conductor.

11. The fluorescence detection device according to claim 7, wherein the conducting layer is more than 20 nm thick.

12. The fluorescence detection device according to claim 1, wherein the support means comprises a spacing layer transparent to the excitation and emission wavelengths involved in the fluorescence process.

13. The fluorescence detection device according to claim 12, wherein the spacing layer is a layer of polymers.

14. The fluorescence detection device according to claim 12, wherein the spacing layer is a ceramic layer.

15. The fluorescence detection device according to claim 12, wherein the spacing layer is more than 20 nm thick.

16. The fluorescence detection device according to claim 1, wherein the spacing layer is about 60 nm thick, the conducting layer is about 60 nm thick and the roughness of the surface of the conducting layer is defined by a standard deviation of roughness of about 20 nm, an average spatial period of roughness of about 350 nm and a range of spatial periods of roughness of about 600 nm.

17. The fluorescence detection device according to claim 12, wherein the spacing layer is arranged with a thickness gradient.

18. The fluorescence detection device according to claim 17, wherein the thickness of the spacing layer increases from a first end of the support means to a second end of the support means.

19. The fluorescence detection device according to claim 1, wherein the excitation means covers an illumination cone.

20. A method of monitoring fluorophores in a sample comprising:
providing the fluorescence detection device according to claim 1;
exciting fluorophores in a sample supported by a support means of the fluorescence detection device so that a fluorescence is emitted by said sample; and
detecting the fluorescence emitted by the excited sample for monitoring fluorophores in the sample.

21. A method of studying inter-fluorophore energy transfers comprising: providing the fluorescence detection device according to claim 1;
exciting fluorophores in a sample supported by a support means of the fluorescence detection device so that a fluorescence is emitted by said sample; and
detecting inter-fluorophore energy transfers.

22. A method of measuring thickness of a sample comprising providing the fluorescence detection device according to claim 1;
exciting a sample supported by a support means of the fluorescence detection device so that a fluorescence is emitted by said sample;
detecting the fluorescence emitted by the excited sample;
measuring displacement of fluorescence intensity; and
calculating the thickness of the sample.

23. The fluorescence detection device according to claim 1, wherein the support means includes a layer having a rough surface for redirecting said fluorescence in a plurality of directions.

24. A method of fluorescence detection comprising:
exciting a sample supported by a support means so that a fluorescence is emitted by said sample; and
detecting said fluorescence emitted by said excited sample wherein said support means comprises a layer having a rough surface for redirecting said fluorescence in a plurality of directions and said fluorescence detection step comprises an observation within a cone to collect the redirected fluorescence in a plurality of directions and said fluorescence detection comprises an observation within a cone to collect the redirected fluorescence in a plurality of directions, and wherein said rough surface has a roughness defined by a standard deviation of roughness and being non-zero and less than 100 nm.

25. A fluorescence detection device comprising a support means for supporting a sample, a sample excitation means so that a fluorescence is emitted by the sample and a detection means for detecting said fluorescence, wherein said support mean comprises a layer having a rough surface for redirecting said fluorescence in a plurality of directions and said detection means covers an observation cone to collect the redirected fluorescence in a plurality of directions, said rough surface having a roughness defined by an average spatial period of roughness, said average spatial period of roughness being derived from the radial profile of the power spectrum of the topography image of the rough surface, and being non-zero and less than 1000 nm.

* * * * *